United States Patent
Reisinger et al.

(10) Patent No.: US 6,852,872 B2
(45) Date of Patent: Feb. 8, 2005

(54) PROCESS FOR PRODUCING DIARYL CARBONATES

(75) Inventors: Claus-Peter Reisinger, Wixom, MI (US); Sven Michael Hansen, Krefeld (DE); Peter Fischer, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 105 days.

(21) Appl. No.: 10/200,667

(22) Filed: Jul. 22, 2002

(65) Prior Publication Data

US 2003/0036663 A1 Feb. 20, 2003

(30) Foreign Application Priority Data

Jul. 27, 2001 (DE) .......................... 101 36 856

(51) Int. Cl.[7] .............................. C07C 69/96
(52) U.S. Cl. ........................................ 558/274
(58) Field of Search ......................... 558/274

(56) References Cited

U.S. PATENT DOCUMENTS

| | | | |
|---|---|---|---|
| 4,201,721 A | 5/1980 | Hallgren | 260/463 |
| 4,349,485 A | 9/1982 | Hallgren | 260/463 |
| 5,231,210 A | 7/1993 | Joyce et al. | 558/274 |
| 5,498,742 A | 3/1996 | Buysch et al. | 558/274 |
| 5,502,232 A * | 3/1996 | Buysch et al. | 558/270 |
| 5,760,272 A | 6/1998 | Pressman et al. | 558/274 |
| 5,821,377 A * | 10/1998 | Buysch et al. | 558/274 |
| 5,898,079 A | 4/1999 | Pressman et al. | 558/274 |
| 5,898,080 A | 4/1999 | Pressman et al. | 558/274 |
| 6,034,262 A | 3/2000 | Moreno | 558/274 |
| 6,180,812 B1 | 1/2001 | Johnson et al. | 558/274 |
| 6,207,849 B1 | 3/2001 | Shalyaev et al. | 558/274 |

* cited by examiner

*Primary Examiner*—Joseph K. McKane
*Assistant Examiner*—Golam M M Shameem
(74) *Attorney, Agent, or Firm*—Joseph C. Gil; Gary F. Matz; Aron Preis

(57) ABSTRACT

A process for producing diaryl carbonate is disclosed. The process entails forming a reaction mixture wherein reacting are an aromatic hydroxy compound corresponding to the formula $$R-O-H \qquad (II),$$

wherein R denotes a $C_{6-22}$-aromatic hydrocarbon radical, with CO and $O_2$ in the presence of a catalyst system. The catalyst system contains components a) a Group VIII B metal compound, b) at least one second metal compound, c) a bromide compound, and d) a base. The process entails introduction of one or more of components a) to d) to the reaction mixture in more than one increment in the course of the reaction.

9 Claims, No Drawings

US 6,852,872 B2

PROCESS FOR PRODUCING DIARYL CARBONATES

FIELD OF THE INVENTION

The present invention is directed to a process for the preparation of diaryl carbonates (DAC) and more particularly to a catalyzed process.

SUMMARY OF THE INVENTION

A process for producing diaryl carbonate is disclosed. The process entails forming a reaction mixture wherein reacting are an aromatic hydroxy compound corresponding to the formula $$R\text{—}O\text{—}H \quad (II),$$

wherein R denotes a $C_{6\text{-}22}$-aromatic hydrocarbon radical, with CO and $O_2$ in the presence of a catalyst system. The catalyst system contains components a) a Group VIII B metal compound, b) at least one second metal compound, c) a bromide compound, and d) a base. The process entails introduction of one or more of components a) to d) to the reaction mixture in more than one increment in the course of the reaction.

BACKGROUND OF THE INVENTION

The production of DAC by oxidative direct carbonylation of aromatic hydroxy compounds in the presence of CO, $O_2$ and of a precious metal catalyst is known (see, for example, DE-OS 27 38 437, U.S. Pat. Nos. 4,349,485, 5,231,210, EP-A 667 336, EP-A 858 991, U.S. Pat. No. 5,760,272). The precious metal used is preferably palladium. In addition, a co-catalyst (for example, manganese salts or cobalt salts), a base, sources of bromide, quaternary salts, various quinones or hydroquinones and drying agents may be used. The reaction may be carried out in a solvent.

However, the known processes do not deliver adequate yields for a technical conversion and produce relatively large quantities of secondary products. It is therefore desirable to provide a process which is optimised with regard to yield and quality of product.

A process has now been found which renders possible a surprising increase in the selectivity of the reaction, i.e. the decrease of secondary products with constant product yield.

DETAILED DESCRIPTION OF THE INVENTION

The invention therefore provides a process for producing an aromatic carbonate corresponding to the formula $$R\text{—}O\text{—}CO\text{—}O\text{—}R \quad (I),$$

wherein

R represents optionally substituted, aromatic hydrocarbon groups, having preferably 6 to 22 carbon atoms, in which an aromatic hydroxy compound corresponding to the formula $$R\text{—}O\text{—}H \quad (II),$$

wherein

R has the same meaning as above,

CO and $O_2$, optionally in a solvent in the presence of a catalyst system comprising the components
a) a Group VIII B metal compound,
b) at least one second metal compound,
c) a bromide compound, and
d) a base
are reacted together, characterized in that one or more of components a) to d) are added to the reaction mixture more than once in the course of the reaction.

The aromatic hydroxy compounds R—O—H according to the invention are, for example, monohydroxy compounds such as phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol or di- or polyhydroxy compounds such as resorcinol and hydroquinone, as well as tris- and bisphenols, such as 2,2-bis(4-hydroxyphenyl)propane (bisphenol A), 2,2-bis(3,5-dimethyl-4-hydroxyphenyl)propane, 1,1-bis(4-hydroxyphenyl)cyclohexane, 1,1-bis(4-hydroxyphenyl)-3,3,5-trimethylcyclohexane or 6,6'-dihydroxy-3,3,3',3'-tetramethyl-1,1'-spiro(bis)indane, 2,4'-hydroxybiphenyl or 4,4'-hydroxybiphenyl. In a case where the aromatic hydroxy compound is substituted, there are one to three substituents, which may be $C_1$–$C_{18}$-alkyl, $C_6$–$C_{18}$-aryl, $C_7$–$C_{18}$-aralkyl, $C_1$–$C_{18}$-alkoxy, fluorine, chlorine or bromine. Preferably monohydroxy compounds are used, particularly preferably phenol.

The Group VIII B metal compound, that is a platinum metal compound a) includes at least one precious metal from Group VIII B, preferably palladium. In the process according to the invention, this may be added in various forms. Palladium may be used in metallic form, for example, as palladium black or on a support such as Pd/C, Pd/$Al_2O_3$, Pd/$SiO_2$ or, preferably, in the form of palladium compounds in the oxidation states 0 and +2, such as, for example, palladium(II) acetylacetonate, palladium halides, palladium carboxylates of $C_2$–$C_{18}$-carboxylic acids, palladium dicarboxylates such as oxalate, palladium nitrate, palladium sulfate, palladium oxides or palladium complexes, which may contain, for example, carbon monoxide, olefins, amines, nitriles, phosphorus compounds and halides. Palladium bromide and palladium acetylacetonate are particularly preferred.

The quantity of platinum metal compound is not limited in the process according to the invention. Preferably this compound—component (a)—is added to the reaction batch in a quantity such that the concentration of the metal in the reaction batch is 1 to 3000 ppm; concentrations of 5 to 500 ppm are particularly preferred.

The metal of the second metal compound b), which acts as a co-catalyst for the process according to the invention, is selected from Groups III A, III B, IV A, IV B, V B, I B, II B, VI B, VII B, from among the rare earth metals (atomic numbers 58–71) or from the iron group of the periodic system of the elements (Mendeleev), optionally also mixtures of these; the metal may be used in various oxidation states (see, for example, U.S. Pat. Nos. 5,142,086, 5,231, 210, 5,284,964, EP-A 350 697, EP-A 350 700, U.S. Pat. No. 5,336,803). Preferably Pb, Ti, Mn, Cu, Co, V, Zn, Ce and Mo are used. Without thereby limiting the process according to the invention, one may mention lead(II), manganese(II), manganese(III), copper(I), copper(II), cobalt(II), cobalt(III), vanadium(III) and vanadium(IV), in particular manganese (II), manganese(III), cobalt(II), cobalt(III). The metals may be used, for example, as halides, oxides, carboxylates of $C_2$–$C_{18}$-carboxylic acids, diketonates or nitrates as well as complex compounds, which may contain, for example, carbon monoxide, olefins, aromatic and aliphatic mono- or polyamines, phosphorus compounds, pyridines, bipyridines, terpyridines, quinolines, isoquinolines, cryptands, Schiff bases and halides. Particularly preferably Mn, Cu, Mo, Pb and Ce are used. It is most preferable to use manganese compounds in the process according to the invention, particularly preferably manganese(II) and manganese(III) complexes, most preferably manganese(II) acetylacetonate or manganese(III) acetylacetonate, as well as manganese(II) bromide.

Component (b) which may also be formed in situ, is added to the reaction batch in a quantity such that its concentration is in the range of 0.0001 to 20 wt. % of the reaction mixture; the concentration range is preferably from 0.001 to 5 wt. %, particularly preferably 0.005 to 2 wt. %.

The bromide compounds c) used in the present invention include for example, the alkali metal bromides or alkaline-earth bromides, but are preferably the bromide salts of organic cations. The organic cations may, for example, be ammonium salts, guanidinium salts, phosphonium salts or sulfonium salts substituted with organic groups and optionally also mixtures of these. Ammonium salts, guanidinium salts, phosphonium salts or sulfonium salts which contain $C_6$- to $C_{10}$-aryl, $C_7$- to $C_{12}$-aralkyl and/or $C_1$- to $C_{20}$-alkyl groups as organic groups are suitable for use in the process according to the invention. Preferably, ammonium salts containing $C_6$- to $C_{10}$-aryl, $C_7$- to $C_{12}$-aralkyl and/or $C_1$- to $C_{20}$-alkyl groups as organic groups are used in the process according to the invention. Tetrabutylammonium bromide and tetrabutylphosphonium bromide are particularly preferred. The quantity of the bromide compound is 0.1 to 20 wt. %, based on the weight of the reaction mixture. This quantity is preferably 0.5 to 15 wt. %, particularly preferably 1 to 5 wt. %.

The usable base, component (d), for the process according to the invention include alkali hydroxides, alkali metal salts or quaternary salts of weak acids such as alkali tert. butoxides or alkali metal salts or quaternary salts of aromatic hydroxy compounds corresponding to formula (II), wherein R has the meaning given above. It is particularly preferable to use an alkali metal salt or quaternary salt of the aromatic hydroxy compound corresponding to formula (II), for example, tetrabutylammonium phenolate or potassium phenolate, which should also be converted to the organic carbonate.

The alkali metal salts may be salts of lithium, sodium, potassium, rubidium or of caesium. Preferably lithium phenolate, sodium phenolate and potassium phenolate are used; potassium phenolate is particularly preferred.

The quaternary salts may be ammonium salts, phosphonium salts, pyridinium salts, sulfonium salts or guanidinium salts which have $C_6$- to $C_{18}$-aryl, $C_7$- to $C_{18}$-aralkyl and/or $C_1$- to $C_{20}$-alkyl groups as organic groups. The groups may all be identical or different, optionally mixtures of several quaternary salts may also be used. Here it is preferable, if possible, that the same cation be used as is used as bromide for component c). Moreover, tetraphenylphosphonium, tetrabutylammonium, tetrabutylphosphonium are preferred; tetrabutylammonium is particularly preferred.

Alternatively, trialkylamine bases such as tributylamine, diisopropylethylamine, DBU, DBN may be used.

The base d) is used in a quantity which is independent of the stoichiometry. The ratio of platinum metal, for example, palladium, to base is preferably so chosen that 0.1 to 5000, preferably 1 to 1000, particularly preferably 10 to 300, equivalents of base are used per mol of platinum metal, for example, palladium.

One or more of components a) to d) may be added to the reaction mixture more than once according to the invention, but such subsequent addition of components a) and/or b) is preferred.

Here, the subsequent addition of Pd compounds and/or manganese salts b) is particularly preferred.

The catalyst components may be subsequently added in portions, once or in several portions. Preferably, one commences with an initial addition, of about 10 to 80 wt. % of the total quantity of catalyst system and the remaining quantity is added as one or more subsequent additions. The amount of catalyst system that is added initially is particularly preferably about 30 to 70 wt. % relative to the total quantity of the catalyst system. The subsequent additions are preferably in at least one and up to about ten increments. The time intervals between the additions are preferably about equal. Preferably the final portion is added at a time prior to about 90%, particularly preferably prior to about 80%, of the total reaction period, or average residence time.

The subsequently added quantity of the component(s) of the catalyst system, that is the quantity introduced after the initial introduction, may also be introduced continuously, for example, by slow pumping of a solution. Here, one commences preferably with an initial addition within the first hour of the reaction period, of about 10 to 80 wt. % of the total quantity and the remaining quantity is then added subsequently and continuously. The initial amount added is particularly preferably about 30 to 70 wt. %. Different schedules of additions, represented by a variety of profiles of time-added amounts may be used; for example, a greater amount of catalyst per unit of time may be added at the beginning than at the end of the reaction period, or vice versa. A linear rate of addition of the remaining quantity of catalyst, in which the added quantity per interval of time remains approximately constant, is preferred. The addition may be commenced and terminated at any time during the reaction or during the average residence time.

The addition is concluded preferably at a time prior to about 90%, particularly preferably prior to about 80%, of the total reaction period, or average residence time.

The process according to the invention may be conducted both continuously and batchwise.

In a batch operation, the components of the catalyst system may be added to the reactor at any time after the beginning of the reaction.

In a continuous operation, for example, in a cascade of n reaction vessels, one or more of components a) to d) may be fed into at least one of the second to nth reactors during the reaction.

The process according to the invention for the formation of carbonate is carried out at a reaction temperature of 30° C. to 200° C., preferably 50° C. to 150° C., particularly preferably 60° C. to 130° C., and at a reaction pressure of 1 to 200 bar, preferably 1 to 50 bar, particularly preferably 1 to 10 bar.

Substances which may be used as inert organic solvent are hydrocarbons, halogenated hydrocarbons and aromatic solvents such as chlorobenzene, dichlorobenzene, fluorobenzene, benzene, toluene, anisole, cyclohexane, petroleum ether, methylene chloride or 1,2-dichloroethane, dipolar aprotic solvents such as dimethylacetamide, acetonitrile, N-methylpyrrolidone, ethers such as dioxan, tetrahydrofuran, t-butyl methyl ether and etherified glycols and optionally mixtures of different solvents. The use of chlorobenzene is particularly preferred. The reaction mixture may contain the inert solvent in a proportion of 1% to 99%, preferably 20% to 98% and particularly preferably 40% to 98%.

The composition of the reaction gases carbon monoxide and oxygen may be varied within wide concentration limits, but it is advisable to establish a $CO:O_2$ molar ratio (standardized against CO) of 1:0.001 to 1:1, preferably 1:0.01 to 1:0.5 and particularly preferably 1:0.02 to 1:0.3. At these molar ratios, the oxygen partial pressure is great enough to enable high space-time yields to be attained.

All reactants may be contaminated with impurities acquired during their production and storage, but in the interest of the purity of the end product it is desirable to use chemicals which are as clean as possible. The reaction gases are not subject to any particular standards of purity either. Thus, synthesis gas may be used as a source of CO and air as an $O_2$ carrier, but care must be taken to ensure that no catalyst poisons such as, for example, sulfur or its compounds are introduced. The gases may be diluted with one or more other gases such as nitrogen, argon, carbon dioxide or hydrogen. In the preferred embodiment of the process according to the invention, pure CO and pure oxygen are used.

In another embodiment, a heterogeneous catalyst system in which the platinum metal compound and/or the cocatalyst of component (b) are applied to a heterogeneous support, are used in the form of powder or mouldings. The remaining components of the catalyst system, such as the base, the quaternary compound and optionally the cocatalyst, are also homogeneously dissolved in the reaction mixture. The quantity of platinum metal in the total weight of the heterogeneous catalyst is 0.01 to 15 wt. %, preferably 0.05 to 10 wt. %, calculated as platinum metal.

At least one metal compound of the type mentioned above is used as a cocatalyst on the catalyst support.

The proportion of the cocatalyst in the total weight of the heterogeneous catalyst is 0.01 to 15 wt. %, preferably 0.05 to 10 wt. %, calculated as metal.

Suitable catalyst supports are one or more oxides of metals selected from V, Mn, Ti, Cu, Zr, La, from the rare-earth metals (atomic numbers 58–71), both as chemically uniform pure substances and as a mixture, as well as iron oxides and cobalt oxides, nickel oxide, aluminium oxide, silicon oxide and magnesium oxide, zeolites and activated carbons. If the catalyst support is used as powder, the agitated tanks to be used are equipped with useful stirrers for the purpose of mixing the reaction components, for example, they may be made into bubble columns.

In the case of an operation using supported-catalyst powders in the form of a suspension in stirrer vessels or bubble columns, quantities of 0.001 to 50 wt. %, preferably of 0.01 to 20 wt. %, particularly preferably of 0.1 to 10 wt. %, of supported-catalyst powder are used, the percents being in relation to the initial quantity of aromatic hydroxy compounds.

In preferred embodiments, the heterogeneous supported catalyst is used in a fixed position in agitated tanks, in a bubble column, a trickle phase reactor or cascades of these reactors. A separation of the supported catalyst is then completely omitted.

Suitable reactors for the process according to the invention using a homogeneous or heterogeneous catalyst are agitated tanks, autoclaves and bubble columns; these may be used as individual reactors or in the form of a cascade. In a cascade, 2 to 15, preferably 2 to 10 and particularly preferably 2 to 5 reactors may be connected in series.

The agitated tanks to be used according to the invention are equipped with suitable stirrers for the purpose of mixing the reaction components. Such stirrers are known to the person skilled in the art. Examples which may be mentioned are: disk agitators, impellers, propellers, blade mixers, MIG and Intermig mixers, tube mixers and various types of cavity mixer. Preferred stirrers are those which permit an effective mixing of gases and liquids, for example, hollow tube gas dispersion stirrers, propellers, etc.

The following types of bubble column may be used in the process according to the invention: simple bubble columns, bubble columns containing built-in units such as, for example: bubble columns with parallel chambers, cascades of bubble columns with perforated plates or single-hole plates, bubble columns with packing, or with static mixers; pulsed sieve-plate bubble columns; loop reactors such as, for example: mammoth loop reactors, descending loop reactors, jet loop reactors, free-jet reactors, jet-nozzle reactors, bubble columns with liquid immersed radiator, descending-ascending bubble columns and other bubble columns known to the person skilled in the art (Chem. Ing. Tech. 51 (1979) No. 3, p. 208–216; W. -D. Deckwer, Reaktionstechnik in Blasensäulen, Otto Salle Verlag 1985).

In a preferred embodiment, bubble columns and bubble column cascades which permit an effective mixing of gases and liquids are used such as, for example, cascades of bubble columns and loop reactors. Devices for distribution and redispersion may be attached along the longitudinal axis of the bubble columns in order to maintain a thorough mixing of liquid and reaction gas. Solid redispersion devices used are single-hole plates, perforated plates, as well as other built-in units known to the person skilled in the art. For the initial dispersion of the reaction gas in the liquid phase during the introduction of the reactants, conventional devices may be used, such as porous sintered plates, perforated plates, inserted tubes, nozzles, gas dispersion rings and other dispersion devices known to the person skilled in the art.

The process according to the invention may be carried out in any of a number of ways. One possibility is a batch operation. Here, CO and oxygen are introduced into the reaction mixture either through a gas dispersion ring, as in the case of an agitated tank, or through other known gas distribution devices. After the optimal conversion has been attained, the reaction mixture is removed from the reactor or optionally processed in the reactor. In the case where pulverulent supported catalysts are used, these may be separated from the reaction mixture, for example, by filtration, sedimentation or centrifugation.

Supported catalysts used in batch experiments may be used repeatedly with identical feed material, optionally without purification. During continuous operation, the supported catalysts used may remain in the reactor for a long time and if necessary be regenerated.

A continuous operation in an individual reactor or in a cascade of several reactors is the preferred procedure. Where fixed heterogeneous catalysts are used, these may remain in the reactor for a long time and also, if necessary, be regenerated there.

EXAMPLES

The reaction components are analysed by gas chromatography, in which the weights of the components may be determined by means of an internal standard. The selectivity is calculated by adding together the quantity of the remaining phenol contained in the reaction mixture and of the phenol converted to DPC and dividing the sum by the total quantity of phenol used. The phenol not included here has been converted into secondary products.

The integral quantity of the catalyst components is defined as integral over the concentration-time curve; the integral Turn Over Frequency (TOF) is the total quantity of DPC in mol produced in 3 hours, divided by the integral quantity of catalyst component.

Example 1

0.12 mmol palladium(II) bromide, 40 mmol tetrabutylammonium bromide, 2.8 mmol manganese trisacetylacetonate and 64 g phenol in 300 g chlorobenzene were placed in an autoclave. Carbon monoxide (<180 Nl/h) was then passed through for 15 minutes at 80° C., after which 40 mmol tetrabutylammonium phenolate in 50 ml chlorobenzene was added. 320 Nl/h of a gaseous mixture of carbon monoxide and oxygen (97.5:2.5 vol. %) was passed through at 90° C./3 bar. In addition, 1.25 mmol manganese trisacetylacetonate in 60 ml chlorobenzene was pumped in continuously and evenly over a period of 120 minutes.

After 1, 2 and 3 hours, a sample was withdrawn and analysed by means of GC.

Comparison Example 1

0.12 mmol palladium(II) bromide, 40 mmol tetrabutylammonium bromide, 4.2 mmol manganese trisacetylacetonate and 64 g phenol in 300 g chlorobenzene were placed in an autoclave at 80° C. Carbon monoxide (<180 Nl/h) was then passed through for 15 minutes at 80° C., after which 40 mmol tetrabutylammonium phenolate in 50 ml chlorobenzene was added. 320 Nl/h of a gaseous mixture of carbon monoxide and oxygen (97.5:2.5 vol. %) was passed through at 90° C./3 bar. After 1, 2 and 3 hours, a sample was withdrawn and analysed by means of GC.

TABLE 1

Subsequent addition of manganese trisacetylacetonate (component b))

| | Time [h] | Quantity of Mn [mmol] | Phenol selectivity [%] | DPC [g] | Integral quantity of Mn [mmol × h] | Integral TOF [mmol (DPC)/ (mol(Mn) × h)/h] |
|---|---|---|---|---|---|---|
| Com Ex. 1 | 0 | 4.20 | 100.0 | 0.0 | 12.6 | 21.0 |
| | 1 | 4.20 | 94.9 | 28.0 | | |
| | 2 | 4.20 | 92.2 | 46.4 | | |
| | 3 | 4.20 | 91.6 | 56.7 | | |
| Ex. 1 | 0 | 2.8 | 100.0 | 0.0 | 10.9 | 23.8 |
| | 1 | 3.21 | 95.8 | 22.3 | | |
| | 2 | 4.05 | 94.5 | 43.8 | | |
| | 3 | 4.05 | 93.8 | 55.6 | | |

Example 2

0.18 mmol palladium(II) bromide, 40 mmol tetrabutylammonium bromide, 2.8 mmol manganese trisacetylacetonate and 64 g phenol in 300 g chlorobenzene were placed in an autoclave at 80° C. Carbon monoxide (<180 Nl/h) was then passed through for 15 minutes, after which 40 mmol tetrabutylammonium phenolate in 50 ml chlorobenzene was added. 320 Nl/h of a gaseous mixture of carbon monoxide and oxygen (97.5:2.5 vol. %) was passed through at 90° C./3 bar. In addition, 0.070 mmol palladium bromide and 0.25 mmol tetrabutylammonium bromide in 108 ml chlorobenzene was pumped in continuously and evenly over a period of 120 minutes. After 1, 2 and 3 hours, a sample was withdrawn and analysed by means of GC.

Comparison Example 2

0.18 mmol palladium(II) bromide, 40 mmol tetrabutylammonium bromide, 2.8 mmol manganese trisacetylacetonate and 64 g phenol in 300 g chlorobenzene were placed in an autoclave at 80° C. Carbon monoxide (<180 Nl/h) was then passed through for 15 minutes, after which 40 mmol tetrabutylammonium phenolate in 50 ml chlorobenzene was added. 320 Nl/h of a gaseous mixture of carbon monoxide and oxygen (97.5:2.5 vol. %) was passed through at 90° C./3 bar. After 1, 2 and 3 hours, a sample was withdrawn and analysed by means of GC.

TABLE 2

Subsequent addition of palladium (component a))

| | Time [h] | Quantity of Pd [mmol] | Phenol selectivity [%] | DPC [g] | Integral quantity of Pd [mmol × h] | Integral TOF [mmol (DPC)/ (mmol(Mn) × h)/h] |
|---|---|---|---|---|---|---|
| Com Ex. 2 | 0 | 0.180 | 100.0 | 0.0 | 0.54 | 458.2 |
| | 1 | 0.180 | 93.9 | 24.3 | | |
| | 2 | 0.180 | 92.6 | 41.9 | | |
| | 3 | 0.180 | 91.8 | 53.0 | | |
| Ex. 2 | 0 | 0.120 | 100.0 | 0.0 | 0.50 | 506.0 |
| | 1 | 0.161 | 93.9 | 22.6 | | |
| | 2 | 0.191 | 93.7 | 44.7 | | |
| | 3 | 0.190 | 93.3 | 54.2 | | |

Example 3

In a continuously operating apparatus comprising 2 cascading autoclaves, 30 mg/kg palladium (as palladium(II) bromide), 250 mg/kg manganese (as manganese(III) trisacetylacetonate), 2 wt. % tetrabutylammonium bromide, 1.8 wt. % tetrabutylammonium phenolate, 16 wt. % phenol and 74 wt. % chlorobenzene were introduced continuously as feed into the first autoclave at 96° C./3 bar (carbon monoxide/oxygen=97.5/2.5 vol. %). In addition, a feed of 10 mg/kg palladium in 0.18 wt. % tetrabutylammonium bromide and 6 wt. % chlorobenzene was introduced into the second autoclave at 110° C. During residence times of approximately 2 hours in each reactor, samples were withdrawn at the outlet of the second reactor and analysed by means of GC. The results are shown in Table 3.

Comparison Example 3

In a continuously operating apparatus comprising 2 cascading autoclaves, similarly to Example 3, 40 mg/kg palladium (as palladium(II) bromide), 250 mg/kg manganese (as manganese(III) trisacetylacetonate), 2 wt. % tetrabutylammonium bromide, 1.8 wt. % tetrabutylammonium phenolate and 16 wt. % phenol, as well as 80.2 wt. % chlorobenzene were introduced continuously into the first autoclave at 96° C./3 bar (carbon monoxide/oxygen=97.5/2.5 vol. %). During residence times of approximately 2 hours in each reactor, samples were withdrawn at the outlet of the second reactor and analysed by means of GC. The results are shown in Table 3.

TABLE 3

Subsequent addition of palladium (component a)) in a continuous procedure

| | Running time [h] | Quantity of Pd [mg/kg] | Phenol selectivity [%] | TON Pd [mmol(DPC)/ (mmol (Pd) × h)/h] |
|---|---|---|---|---|
| Comp. Ex. 3 | 21 | 40 | 84.0 | 1171 |
| Ex. 3 | 32 | 40 | 85.0 | 1153 |

TABLE 3-continued

Subsequent addition of palladium
(component a)) in a continuous procedure

|  | Running time [h] | Quantity of Pd [mg/kg] | Phenol selectivity [%] | TON Pd [mmol(DPC)/ (mmol (Pd) × h)/h] |
|---|---|---|---|---|
| Ex. 3 | 22 | 30 + 10 | 87.3 | 1278 |
|  | 30 | 30 + 10 | 86.8 | 1217 |

The Examples show, surprisingly, that the activity and selectivity of the catalyst components are increased by the subsequent addition according to the invention.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for producing diaryl carbonate corresponding to the formula $$R\text{—}O\text{—}CO\text{—}O\text{—}R \qquad (I),$$

comprising forming a reaction mixture of and reacting an aromatic hydroxy compound corresponding to the formula $$R\text{—}O\text{—}H \qquad (II),$$

wherein
R denotes a $C_{6\text{-}22}$-aromatic hydrocarbon radical, with CO and $O_2$ in the presence of a catalyst system containing components
a) a Group VIII B metal compound,
b) at least one second metal compound,
c) a bromide compound, and
d) a base, and
wherein at least one of components a) and b) are added to the reaction mixture in more than one increment in the course of the reaction.

2. The process of claim 1 wherein component (a) is added to the reaction mixture in more than one increment.

3. The process according to claim 1 wherein the metal of component (b) is a member selected from the group consisting of lead, cerium, cobalt, copper, titanium, zinc, molybdenum, manganese and vanadium.

4. The process of claim 1 wherein component (b) is added to the reaction mixture in more than one increment.

5. The process according to claim 1 wherein diaryl carbonate is diphenyl carbonate.

6. The process according to claim 1 wherein at least one of components a) and b) are added to the reaction mixture in one to ten increments.

7. The process according to claim 1, wherein about 10 to 80% of the total quantity of at least one of components a) to d) is added during the first hour of the reaction period.

8. The process according to claim 7 wherein 20 to 90% of at least one of components a) to d) is continuously added to the reaction mixture of the first hour of the reaction period.

9. A continuous process for the production of diaryl carbonates corresponding to the formula $$R\text{—}O\text{—}CO\text{—}O\text{—}R \qquad (I)$$

in a cascade containing a first reaction vessel and a plurality of subsequent reaction vessels, comprising forming a reaction mixture of and reacting an aromatic hydroxy compound corresponding to the formula $$R\text{—}O\text{—}H \qquad (II),$$

wherein
R denotes a $C_{6\text{-}22}$-aromatic hydrocarbon radical, with CO and $O_2$ in the presence of a catalyst system containing components
a) a Group VIII B metal compound,
b) at least one second metal compound,
c) a bromide compound, and
d) a base
wherein at least one of components a) to are fed into said first reaction vessel and at least one subsequent reaction vessel in the course of the reaction.

* * * * *